United States Patent [19]

Quinlan

[11] 4,074,999
[45] Feb. 21, 1978

[54] USE OF CYCLIC THIAZINES AS MICROBIOCIDES

[75] Inventor: Patrick M. Quinlan, Webster Groves, Mo.

[73] Assignee: Petrolite Corporation, St. Louis, Mo.

[21] Appl. No.: 364,747

[22] Filed: May 29, 1973

Related U.S. Application Data

[62] Division of Ser. No. 119,387, Feb. 26, 1971, Pat. No. 3,770,732.

[51] Int. Cl.² ............................................. A01N 9/22
[52] U.S. Cl. ...................................................... 71/67
[58] Field of Search ....................... 71/91, 67; 424/246

[56] References Cited

U.S. PATENT DOCUMENTS 2,729,636  1/1956  Erickson .............................. 260/243

Primary Examiner—Lewis Gotts
Assistant Examiner—Catherine L. Mills
Attorney, Agent, or Firm—Sidney B. Ring; Hyman F. Glass

[57] ABSTRACT

Cyclic thiazines of the formula

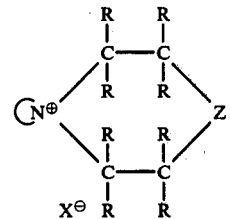

where the R's are hydrogen or a substituted group such as a hydrocarbon group, i.e., alkyl, etc. and N is a cyclic moiety, Z is S,

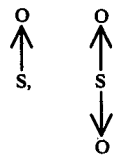

and X is an anion, are prepared by reacting a cyclic secondary amine salt with a divinyl sulfur compound. These are illustrated by the reaction of piperidine hydrochloride with divinyl sulfone to yield

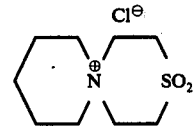

These products have a wide variety of uses including their use as microbiocides, etc.

10 Claims, No Drawings

USE OF CYCLIC THIAZINES AS MICROBIOCIDES

This Application is a division of my pending application Ser. No. 119,387, filed on Feb. 26, 1971 and entitled "CYCLIC THIAZINES" now U.S. Pat. No. 3,770,732, patented Nov. 6, 1973.

This invention relates to cyclic thiazine compounds of the formula

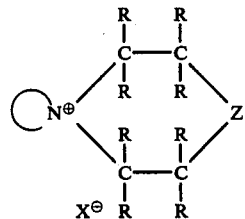

where the R's are hydrogen or a substituted group such as a hydrocarbon group, i.e., alkyl, etc., and N is a cyclic moiety, Z is S, S → O, O ← S → O and X is an anion. These compounds are prepared by reacting a divinyl sulfur compound with a cyclic secondary amine.

The reaction may be summarized by the following equation:

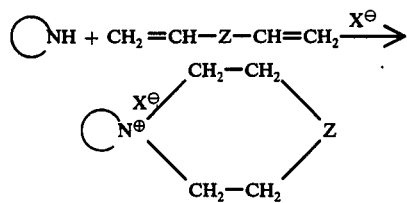

Examples of the divinyl sulfur compounds are:

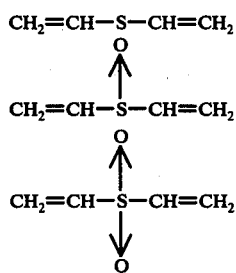

Examples of cyclic amines include any cyclic secondary amine capable of reacting with a divinyl sulfur to form the compounds of this invention, for example:

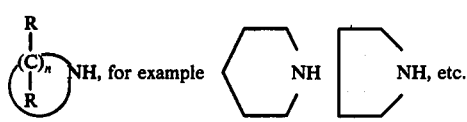

where the R's, which may be the same or different, are hydrogen or a substituted group such as a hydrocarbon, i.e., alkyl, etc., and n is a number, preferably 5-7, most preferably 6.

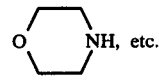 where Z is S, S, S,

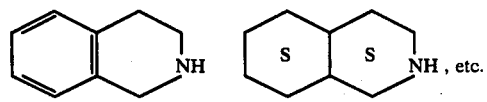

Also, included within the scope of the invention are polycyclic amines including hydrocarbon amines and hydrocarbon amines having other elements present, such as sulfur, oxygen, etc., for example, The following are illustrative examples of cyclic amines.
- Morpholine
- Piperidine
- Pyrrolidine
- Azetidine
- Thiomorpholine
- N-ethyl piperazine
- N-hydroxyethyl piperazine
- Hexahydroazepine Suitable acids that may be employed to form the amine salts include hydrohalic acids such as hydrochloric, hydrobromic, hydroiodic, etc; sulfuric, phosphoric, nitric, perchloric, hydrocarbon sulfonic acids such as methanesulfonic, ethyl sulfonic, benzyl sulfonic, and the like.

In carrying out the reaction it is preferred to form the amine salt in situ, that is in a solvent such as ethanol in which it is soluble. However, if desired, the salt may first be isolated and purified. To the solution of the amine salt in a suitable inert solvent is added the divinyl sulfone. The preferred temperature is about 20° to 50° C. though higher or lower temperatures may be employed. A catalyst such as triethylamine may be used. In most instances the thiazine dioxide quaternary nitrogen salt precipitates from the alcoholic medium and is purified by recrystallization. In some cases it is necessary to reduce the final volume in order to isolate the desired product.

The invention may be illustrated by the following examples:

EXAMPLE 1

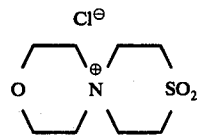

Divinyl sulfone 5.9 g. (0.05 mole) was slowly added to a solution of 13 g. (0.15 mole) of morpholine in 25 ml. of 4 N ethanolic hydrochloric acid. The reaction mixture became warm and crystals appeared. After 24 hours the crystalline product was filtered and washed with alcohol; yield 8.2 g. (65% of theory) m.p. 287°–289° (decomp).

Analysis: Calculated for $C_8H_{16}ClNO_3S$: C, 39.83; H, 6.62; Cl, 14.67; S, 13.22; N, 5.80.

Found: C, 39.94; H, 6.80; Cl, 14.76; S, 13.33; N, 5.84.

IR and NMR spectra were used to characterize and verify the above structure.

EXAMPLE 2

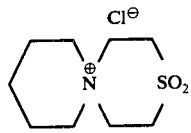

Divinyl sulfone 5.9 g. (0.05 mole) was slowly added to a solution of 12.8 g (0.15 mole) of piperidine in 25 ml of 4 N ethanolic hydrochloric acid. The reaction mixture became warm and crystals appeared upon cooling. After 24 hours, the colorless crystalline product was filtered and washed with alcohol. It was recrystallized from aqueous ethanol; yield 9.0 g. (75% of theory); m.p. 287°–289° (decomp).

Analysis: Calculated for $C_9H_{18}ClNO_2S$: C, 45.0; H, 7.55; Cl, 14.78; N, 5.85; S, 13.3.

Found: C, 46.0; H, 7.74; Cl, 15.00; N, 5.71; S, 13.58.

IR and NMR spectra were used to identify the above structure.

EXAMPLE 3

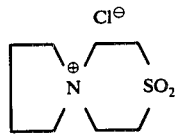

Divinyl sulfone 5.9 g. (0.05 mole) and a few drops of triethyl amine were added to a solution of 10.8 g (0.15 mole) of pyrrolidine in 25 ml of 4 N ethanolic hydrochloric acid. The reaction mixture became warm and crystals appeared upon cooling. After 24 hours, the crystalline product was filtered and washed with alcohol. It was recrystallized twice from aqueous ethanol; yield 8.3 g. (73% of theory) m.p. 307°–309° (decomp).

Analysis: Calculated for $C_8H_{16}ClNO_2S$: C, 42.66; H, 7.11; Cl, 15.70; N, 6.21; S, 14.20.

Found: C, 42.67; H, 7.32; Cl, 15.74; N, 6.16; S, 14.44.

EXAMPLE 4

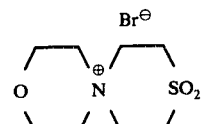

Divinyl sulfone 5.9 g. (0.05 mole) was added to a solution of 13.0 (0.15 mole) of morpholine in 30 ml of ethanol that had been acidified with hydrobromic acid. The reaction mixture became very warm and crystals appeared. The crystalline product was filtered and washed with alcohol. The product was a colorless crystalline product. It was recrystallized from aqueous ethanol.

Analysis: Calculated for $C_8H_{16}BrNO_3S$: Br, 27.8; N, 4.9.

Found: Br, 26.6; N, 4.7.

In a similar manner the following examples were prepared.

| Example | Structure | $X^{\ominus}$ |
|---|---|---|
| 5 | O-N | I |
| 6 | N | I |
| 7 | N | Br |
| 8 | S-N | Cl |
| 9 | $C_2H_5$—N N | Cl |
| 10 | N | Br |

Thus, the composition of this invention may be summarized by the formula

where ◯N is a cyclic amino group and ◯X is a cyclic group where X is S,

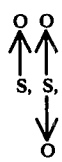

for example of the formula

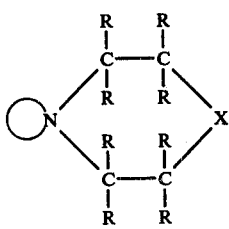

where the R's are hydrogen or hydrocarbon such as alkyl, etc., and most preferably

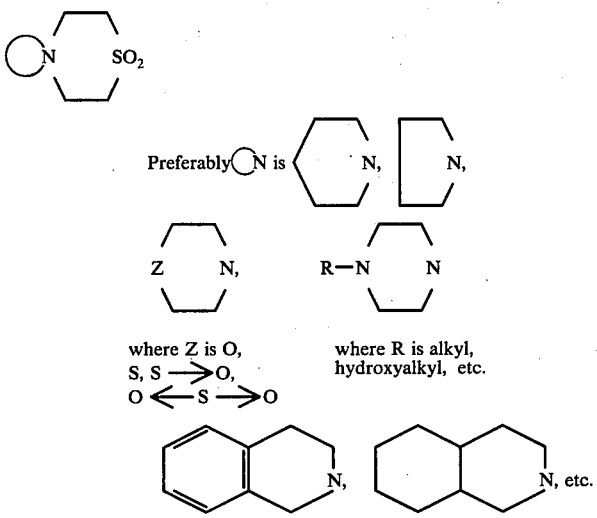

USE AS A MICROBIOCIDE

I. In Water Treatment

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algae, protozoa and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bactericidal, fungicidal and algicidal. They further provide a simple process whereby water supplies for whatever purposes intended, are rendered bacteriostatic, fungistatic and algistatic, i.e., said water supplies treated by the process of this invention will resist and inhibit the further growth or proliferation of bacteria, fungi, algae and all forms of microbial life therein.

II. Water Flooding in Secondary Recovery of Oil

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond the 20 - 30 percent of the oil in a producing formation that is usually recovered in the primary process. In flooding operations, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil bearing formations seriously reduces the efficiency of the recovery operation.

The term "flood water" as herein employed is any water injected into oil-bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and-/or existing in sufficiently high numbers to constitute an appreciable mass, thereby plugging the pores of the oil-bearing formation. Pore-plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

Organisms of the Desulfovibrio genus, more commonly known as sulfate reducing bacteria, are known particularly to preclude efficient operation of oil recovery by conventional water flooding techniques by producing $H_2S$ which reacts with iron or iron salts to precipitate black ferrous sulfide. These organisms are often resistant to the effects of many known antimicrobial compounds.

I have discovered that the compositions of this invention are effective bactericides for sulfate reducing bacteria.

III. Hydrocarbon Treatment

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

Microbiocidal Testing

The screening procedure was as follows: a one percent by weight solution of the test compound in water was prepared. The solution was aseptically added to a sterile broth that would support the growth of the test organism, Desulfovibro desulfuricans, to provide a concentration of 50 and 100 parts by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 24 hours. The absence or presence of growth of the microorganisms was determined by visual inspection by an experienced observer.

Following is a summary of the results of the testing of examples of this invention.

| Compound Example | Concentration of Test Compound |
|---|---|
| (1) | 50 |
| (2) | 50 |
| (3) | 50 |
| (4) | 50 |
| (5) | 50 |
| (6) | 50 |
| (7) | 50 |
| (8) | 100 |
| (9) | 100 |
| (10) | 50 |

In all of the above tests no growth of the test organism occurred, thus indicating that the compound is a biostatic or a biocide.

As is quite evident, other secondary cyclic amines and divinyl sulfur compounds will be constantly developed which could be useful in this invention. It is, therefore, not only impossible to attempt a comprehensive catalogue of such compounds, but to attempt to describe the invention in its broader aspects in terms of other specific compounds used would be too voluminous and unnecessary since one skilled in the art could by following the description of the invention herein select useful cyclic amines and divinyl sulfur compounds. To precisely define each specific useful secondary cyclic amine and divinyl sulfur compound in light of the present disclosure would merely call for chemical knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific compounds suitable for this invention by applying them in the invention set forth herein. In analogy to the case of a machine, wherein the use of certain materials of construction or dimensions of parts would lead to no practical useful result, various materials will be rejected as inapplicable where others would be operative. I can obviously assume that no one will wish to employ a useless compound nor will be misled because it is possible to misapply the teachings of the present disclosure to do so.

I claim:

1. The process of inhibiting and controlling the growth of microbiological organisms selected from the group consisting of bacteria, fungi, algae and protozoa in aqueous or petroleum hydrocarbon media which comprises adding to said media a microbiocidal quantity of a quaternary bicyclic compound of the formula

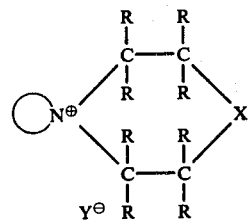

where ◯N is

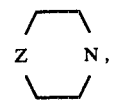

where Z is O, S, S←O or O←S→O, or

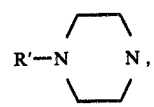

where R' is lower alkyl, or hydroxyloweralkyl,

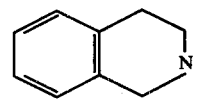 or 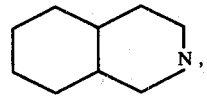

-continued

X is S, 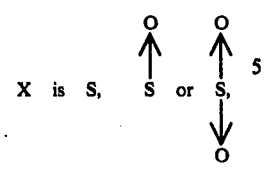

Y is a halide, sulfate, phosphate, nitrate, perchlorate or methane sulfonate, ethyl sulfonate or benzyl sulfonate, and the R's are hydrogen or lower alkyl.

2. The process of claim 1 wherein the quaternary bicyclic compound is of the formula

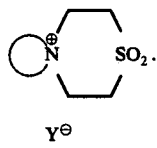

3. The process of claim 2 wherein the quaternary bicyclic compound is of the formula

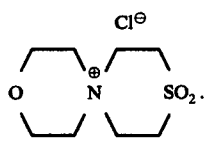

4. The process of claim 2 wherein the quaternary bicyclic compound is of the formula

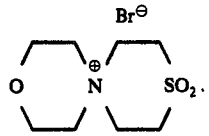

5. The process of claim 2 wherein the quaternary bicyclic compound is of the formula

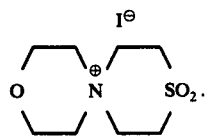

6. The process of claim 2 wherein the quaternary bicyclic compound is of the formula

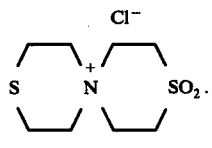

7. The process of claim 2 wherein the quaternary bicyclic compound is of the formula

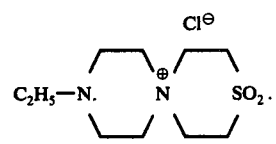

8. The process of claim 1 wherein the media is water.
9. The process of claim 1 wherein the media is a petroleum hydrocarbon.
10. The process of claim 1 wherein the microbiological organism is *Desulfovibro desulfuricans.*

* * * * *